United States Patent [19]

Carter et al.

[11] Patent Number: 5,780,239
[45] Date of Patent: Jul. 14, 1998

[54] METHOD FOR THE DETERMINATION OF CAST IN URINE

[76] Inventors: Jesse M. Carter, 9105 S. Rome Ave.. Tampa, Fla. 33606; Jack V. Smith, 8505 42nd Ave. N., St. Petersburg, Fla. 33709

[21] Appl. No.: 675,386

[22] Filed: Jul. 2, 1996

Related U.S. Application Data

[63] Continuation-in-part of Ser. No. 347,124, Nov. 23, 1994, abandoned.

[51] Int. Cl.⁶ ............................................. G01N 33/53
[52] U.S. Cl. ....................... 435/7.1; 435/7.9; 436/518; 436/87
[58] Field of Search .......................... 435/4, 7.1, 7.21, 435/7.92, 23, 7.9, 805, 970, 7.93, 7.94, 11, 12, 14, 15, 18, 21, 25, 26; 436/518, 530, 531, 63, 169, 180, 87; 422/56

[56] References Cited

U.S. PATENT DOCUMENTS

| | | | |
|---|---|---|---|
| 3,622,463 | 11/1971 | Iizuka et al. | |
| 4,446,232 | 5/1984 | Liotta | 435/7.92 |
| 4,575,486 | 3/1986 | Laird | 435/7.9 |
| 4,690,891 | 9/1987 | Hou et al. | 435/42 |
| 4,786,589 | 11/1988 | Rounds | 435/5 |
| 4,960,710 | 10/1990 | Lau | 436/86 |
| 5,075,078 | 12/1991 | Osikowicz et al. | 422/56 |
| 5,310,655 | 5/1994 | Zimmerhackl et al. | 435/7.9 |
| 5,451,520 | 9/1995 | Furukawa et al. | 435/227 |
| 5,516,700 | 5/1996 | Smith et al. | 436/164 |

OTHER PUBLICATIONS

Cohen et al., "Myeloma Kidney: An Immunomorphogenetic Study of Renal Biopsies," Laboratory Investigation 42(2) 248–256, 1980.

Cohen et al., "Morphology of Renal Tubular Hyaline Casts," Laboratory Investigation, 44(3) 280–287, 1981.

Hoyer et al, "Tamm–Horsfall Glycoprotein Ultrastructural Immunoperoxidase Localization in Rat Kidney," Laboratory Investigation 41(2): 168–173, 1979.

Uto et al., "Determination of Urinary Tamm–Horsfall Protein by ELISA Using of . . . ." Journal of Immunological Methods 138: 87–94, 1991.

Imai et al., "Immunofluorescence Studies of Urinary Casts," Chemical Abstracts 88(18): No. 132894, on p. 218, 1978.

Yin et al., "Urinary Tamm–Horsfall Protein Coating of Free Cells and its Clinical Diagnostic Signficance," Medline Abstract 91323165, 1991.

*Primary Examiner*—Carol A. Spiegel

[57] ABSTRACT

Method for detecting casts in urine by measuring Tamm-Horsfall protein by solid and liquid phase reagents including a method for manufacturing a enzyme specific for Tamm-Horsfall protein which produces a detectable response in the presence of casts in urine.

1 Claim, No Drawings

5,780,239

METHOD FOR THE DETERMINATION OF CAST IN URINE

PRIOR APPLICATIONS

This application is a continuation in part of application Ser. No. 08/347,124, filed Nov. 23, 1994, now abandoned.

BACKGROUND OF THE INVENTION

The present invention is concerned with a method for the sensitive, precise, economical and rapid detection of very small amounts of casts in urine.

The detection of small amounts of casts, which are invisible to the naked eye, in urine is very important for the diagnosis of renal disease, for example, casts are the only elements found in the urinary sediment that are unique to the kidney and are formed primarily within the lumen of the distal convoluted tubule and collecting duct providing a microscopic view within the nephron of the kidney$_1$. The presence of casts is one of the single most important clinical indicators of renal disease. The early detection of casts has dire consequences. The presence of cellular casts is usually indicative of serious renal disease$_1$. The major constituent of casts is Tamm-Horsfall protein, a glycoprotein$_1$. The following table 1.0 shows some of the types of cast present in urine and the clinical significance of their presence.

References: 1. Strasinger, S. K.: Urinalysis and Body Fluids. F. A. Davis, Philadelphia, 1985.

TABLE 1.0

Summary of Urine Casts

| TYPE | Clinical Significance |
| --- | --- |
| Hyaline | Glomerulonephritis, Pyelonephritis, Chronic renal disease, Congestive heart failure |
| Red Blood Cell | Glomerulonephritis |
| White Blood Cell | Pyelonephritis |
| Epithelial Cell | Renal tubular damage |
| Granular | Glomerulonephritis, Pyelonephritis |
| Waxy | Stasis of urine flow |
| Fatty | Nephrotic syndrome |
| Broad Cast | Extreme stasis of flow |

The detection of these casts is important for the diagnosis of diseases and infections of the kidney and urinary tract.

The presence of Tamm-Horsfall protein (THP), a glycoprotein, in urine is especially suitable for a sensitive detection of all casts. Historically testing for the presence of glycoproteins has been through the use of electrophoresis (the process by which charged particles suspended in a solution may be separated through the application of an electric current). This reaction has been used for many years in medicinal and forensic analysis. The chemical reaction is, as a rule, carried out in an electrophoresis chamber on electrophoretic media (gels). Another method for the detection of cast in urine has been microscopic analysis of a few microliters of urine. This method has many drawbacks, one being that the method is very labor intensive and based on subjective interpretation by the microscopist. Multiple independent research indicates that the accuracy of the method of detection of casts by microscopy is in question due to type of light source used, skill of the technician, and inherent difficulty of cast identification among other problems. Microscopy on urine for the identification of casts is reported as cast per low powered field. One low powered field is approximately 5 uL of urine.

A thorough search of patents and research revealed no relative art (i.e., prior art) showing any correlation to this technology. The art of manual microscopic analysis aside, no chemical test means has been described prior to this art for this method. However, the following art will be mentioned to further illustrate the novelty of the present art and the advancement to the art the present device yields. The following patents with the exception of U.S. Pat. No. 4,575,486, do not mention any use of urine as the matrix for detecting specific analytes of interest. It is known in the art that the urine matrix is very complex and consists of many urinary constituents which create strong buffering and interference problems (cannibal like enzymes such as protease) that have to be overcome to provide a method that can be used for the general population with precision and accuracy. The mere mention of a technique that can test a fluid does not include the area of complex fluids such as urine and cannot be used in the same context.

U.S. Pat. No. 4,575,486, claims the detection of red and white blood cells coated with Tamm-Horsfall Protein (THP) for the purposes of trying to determine the origination of red and white blood cells. This patent claims to be able to do this by the use of an antibody to form antibody-antigen complexes that are detected by visual, fluorescent or radioactive techniques in a liquid reagent. This patent is fatally flawed and is of little if any clinical value because it is known in the art that normal urine is supposed to be free of RBC'S, WBC's and other cellular constituents and only a minute amount of THP coated RBC'S and WBC's ever enter the urinary tract. On the other hand, most of the RBC's and WBC's found in urine usually come from urinary tract infections found in the bladder or urethra and/or vaginal discharge. These cells are not THP coated. This makes the detection of THP coated red and white blood cells improbable if not impossible by this method. This patent does not mention anywhere in the disclosure a method for the determination of cast in urine. This patent also fails to mention any use of ultra-violet, calorimetric, spectrophotometric and reflectance techniques for the determination of cast in urine by the use of dipsticks for manual determination or liquid formula that can be used on an automated instrument. This disclosure also fails to mention any modes of determination of urinary cast by any measurable detectable means such as enzymatic, antibody-antigen or calorimetric.

Another patent, U.S. Pat. No. 3,961,039, is a urinary sediment stain for staining urinary particulates onto a glass slide and does not teach or suggest the method of determining the presence of cast in urine by the use of a dipstick or liquid reagent compatible with automated analyzers. This technique cannot be used for dipstick or automated analyzer and if attempted on an automated instrument would destroy its optics and cuvettes. This patent fails to disclose any use of fluorescent, radioactive, ultra-violet, calorimetric, spectrophotometric and reflectance techniques for the determination of cast in urine by the use of dipsticks for manual determination or liquid formula that can be used on an automated instrument. This disclosure also fails to mention any modes of determination of urinary cast by any measurable detectable means such as enzymatic, antibody-antigen, calorimetric or other chemical means.

Another patent, U.S. Pat. No. 4,446,232, is an enzyme immunoassay technique using detection zones for the determination of the presence of antibodies and does not teach or suggest the method of determining the presence of cast in urine by the use of a dipstick or liquid reagent compatible with automated analyzers. Although this obviously has no bearing on the present device, this method fails even to remotely disclose anywhere in the disclosure a method for the determination of cast in urine. This patent also fails to mention any use of ultra-violet, calorimetric, spectrophotometric and reflectance techniques for the determination of cast in urine by the use of dipsticks for manual determination or liquid formula that can be used on an automated instrument. This disclosure also fails to mention any modes of determination of urinary cast by any measurable detectable means such as enzymatic, antibody-antigen, calorimetric, or other chemical means.

Another patent, U.S. Pat. No. 4,786,589, is a immunoassay using formazan-prelabled reactants and does not teach or suggest the method of determining the presence of cast in urine by the use of a dipstick or liquid reagent compatible with automated analyzers. In other words the sample to be assayed has to be premixed with a prelabled primary protein having a specific affinity for the protein of interest. This patent does mention dipsticks, however it also requires the sample to be pretreated with the prelabled protein. This obviously cannot be used by any automated or manual means for the quantitative determination of any urinary constituents due to predilution of sample matrix, lack of sensitivity, the immense labor that would be involved in using this assay in such a postulated form and is not an advancement in the art of detection of cast such as the present device but a step backwards. Again, this patent obviously has no bearing on the present device, this method fails even to remotely disclose anywhere in the disclosure a method for the determination of cast in urine. This patent also fails to mention any use of ultra-violet, calorimetric, spectrophotometric and reflectance techniques for the determination of cast in urine by the use of dipsticks for manual determination or liquid formula that can be used on an automated instrument. This disclosure also fails to mention any modes of determination of urinary cast by any measurable detectable means such as enzymatic, antibody- antigen, calorimetric, or other chemical means.

Another patent, U.S. Pat. No. 3,603,957, mentions the use of assay test strips but again fails to remotely disclose anywhere in the disclosure a method for the determination of cast in urine. This patent also fails to mention any use of ultra-violet, calorimetric, spectrophotometric and reflectance techniques for the determination of cast in urine by the use of dipsticks for manual determination or liquid formula that can be used on an automated instrument. This disclosure also fails to mention any modes of determination of urinary cast by any measurable detectable means such as enzymatic, antibody-antigen, calorimetric, or other chemical means.

In the literature and prior art, there are techniques such as ELISA and other methods that have been used to detect THP, however these methods like the microscope previously mentioned have no relevant bearing on the present device. In the art, ELISA for instance, is a technique that coats a micro-titer well plate with antibody and then is measured for the particular analyte of interest. This immobilized method has no similarity or relevance to dipstick or liquid reagent for automated instruments. It would be impossible to grind up a micro-well titer plate and somehow put it into a liquid fluid by possibly dissolving the plastic plate with an organic solvent making it mobile, then inject this solution into an automated instrument for the quantitative determination of urinary cast or place this solution onto a dipstick and let it dry, then dip this into a urine and then be able to measure it by reflectance or some other detectable means. The afore mentioned techniques, along with two-site immunochemiluminometric techniques, have no bearing on the present device for obvious reasons, for instance, the ELISA is an immobilized method, meaning the technique cannot move from one area to another (like a carrier-free reagent designed to be transferred from a reagent container to a reaction cuvette) thus making these techniques unavailable or applicable to the present device. The mentioned two-site immunochemiluminometric techniques can measure THP by first, again, pretreating the samples with a specific binding protein for THP then the bound and free fractions are separated by yet another antibody and linked to magnetic particles measured by a detectable means. First these techniques are immensely time consuming and the present devices are designed to advance the art by allowing automation and ease of use. The present device is not obvious or remotely comparable to techniques such as mentioned in the prior art or ELISA, microscopic, electrophoresis, two-site immunochemiluminometrics, immunofluorescent staining, zone detection, slide staining, mutiple detection layers, etc., and it would be impossible to do so because of basic scientific differences in the principles of the techniques mentioned. For example, an immobilized ELISA plate versus a liquid reagent that is carrier-free (mobile) and can be transferred through an automated instrument for quantitative analysis of urinary cast while simultaneously being compared to reference standards of known concentrations are not comparable.

SUMMARY OF THE INVENTION

Rapid tests are usually absorbent carriers, preferably papers, which have been impregnated with all of the reagents necessary for the detection reaction (referred to hereafter as dipsticks). After simply dipping them into a body fluid, they show a color reaction. Because of the importance of achieving rapid results, dipsticks have been developed to detect various disease markers in body fluids. Even faster methods, automated liquid chemistry tests, are liquid carrier free media such as water which contain all of the reagents necessary for the determination of the presence of cast (THP).

For the detection of casts, the sensitivity of the test is of decisive importance, and furthermore, it is also desirable. The dipstick test has a qualitative to semi-quantitative sensitivity range of approximately 3 to 5 cast per low powered field (NOTE: one LPF (low powered field) is equivalent to approximately 5.37 uL of urine). On the other hand, the automated liquid test is 3 to 5 times more sensitive than the dipstick method for the detection of cast in the range of 0.10 to 1.35 casts per low powered field or per 5.37 uL.

DETAILED DESCRIPTION OF THE INVENTION

The instant invention provides test strips or automated liquid chemistries (automated urine chemistries for the determination of urinary constituents can be represented by dipsticks and liquid chemistries) for the detection of casts with a hitherto unachievable high sensitivity. Essentially, the present invention comprises test strips (carrier dependent) or liquid reagents (carrier independent) comprising as the indicator, organic compounds selected from the group consisting of a THP (glycoprotein) specific indicator, an Ion-exchange indicator, an Enzyme-labeled THP antigen, an Enzyme-labeled anti-THP antibody, a Chromogenic acceptor, a Chromogenic donor, and an Enzyme capable of using THP as a substrate. These organic compounds are discussed below.

Wherein for the dipstick rapid test an indicator that is specific for the Tamm-Horsfall protein (glycoprotein) is preferred which has a measurable test means (i.e., visual, reflectance, calorimetric, ion-exchange, etc.), an indicator for the liquid chemistry rapid test that is specific for Tamm-Horsfall protein (glycoprotein) is preferred which has a measurable test means (i.e., visual, ultra-violet (UV), reflectance, spectrophotomeric, ion-exchange, antigen-antibody, enzymatic, calorimetric, etc.).

In the following, there are given examples of the most important groups of compounds (indicators and essential system components) comprising a variety of THP assay systems coming within the scope of general formula for dipstick and liquid chemistry rapid test for casts; the individual compounds that make up the rest of the formulas are all known from the literature:

I. 1. Indicators (THP (glycoprotein) specific)—when in the presence of THP the indicator binds with THP and yields a detectable response by ultra-violet, calorimetric, spectrophotometric analysis. The preferred THP specific indicators are THP blue, THP red, THP green, THP yellow, among others. These indicators are obtained by synthesis, for illustrative purposes, THP is introduced to t-Butyloxymethyl (BOC-on) and alanine para-nitroanilide, a complex is formed (BOC-THP-paranitroanilide), THP yellow. This substrate then in the presence of THPase will release nitroanilide and a yellow color is developed. Thus with the THP yellow indicator present the amount of corresponding THP can be determined by the change in change in color which can be measured visually, UV, spectrophotometrically, ionically, calorimetrically and with reflectance.

2. Ion-exchange indicators—when in the presence of THP the indicator releases a hydrogen or other ion into solution once the indicator has come into contact with the THP and binds with it. This ion then reacts preferably with a pH sensitive indicator (such as Thymol blue, Bromcresol green, Bromothymol blue, among others) and yields a detectable color which can be quantitatively measured and compared to known reference standards. The preferred ion-exchange indicators are, ala-THP polyvinyl chloride and ala-Tamm-Horsfall ethyleneglycol-bis(beta-aminoethyl ether)N,N,N',N'-tetraacetic acid, among others. These indicators are obtained by synthesis, for illustrative purposes, THP is introduced to 9-Flurenylmethyloxycarbonyl (FMOC) alanine polyvinyl chloride a complex is formed (FMOC-ala-THP-polyvinyl chloride) ala-THP-polyvinyl chloride. This substrate then in the presence of THPase will release a hydrogen ion in the presence of other ions in solution. Thus, with a pH indicator present the amount of THP can be determined by the change in pH as indicated by the pH indicator's corresponding change in color which can be measured visually, UV, spectrophotometrically, ionically, calorimetrically and with reflectance.

3. Enzyme-labeled antibodies or antigens (indicators)— antibodies for THP are known in the art. It is also known in the art that antibodies can be labeled. The preferred antibody label in the present device can be labeled with nicotinamide adenine dinucleotide phosphate, reduced form (NADPH), nicotinamide adenine dinucleotide phosphate (NADP+), nicotinamide adenine dinucleotide (NAD), nicotinamide adenine dinucleotide, reduced form (NADH), glucose-6-phosphate dehydrogenase (G-6-PDH), alkaline phosphatase, glycerol kinase, beta-delta-galactosidase, C-reactive protein, N- acetylneuraminic acid aldolase, Acyl-CoA oxidase, Acyl-CoA synthetase, Acylpolyamine amidohydrolase, Alcohol oxidase, Alkaline phosphatase, Alkalophilic proteinase, Ascorbate oxidase, cholesterol esterase, cholesterol oxidase, choline oxidase, creatine amidinohydrolase, Creatinine amidohydrolase, creatinine diminase, Diaphorase, Formaldehyde dehydrogenase, delta-Fructose dehydrogenase, Galactose oxidase, beta-Glactosidase, Glucose dehydrogenase, Glucose oxidase, alpha-Glucosidase, beta-Glucosidase, Glutamate dehydrogenase, Glutathione peroxidase, Glucoamlyase, Glycerol dehydrogenase, Glycerol-3-phosphate dehydrogenase, Glycerol kinase, Glycerophosphate oxidase, Hexokinase, para-Hydroxybenzoate hydroxylase, delta-3-Hydroxybutyrate dehydrogenase, Invertase, lactate dehydrogenase, Leucine dehydrogenase, Lipoprotein lipase, Lipase, Amylase, Luciferase, Malate dehydrogenase, Mannitol dehydrogenase, NADPH oxidoreductase, Neuraminidase, Peroxidase, Urease, Uricase, Xanthine oxidase, europium chelate, Protease or other label. For example, in the analysis of urine for THP on an automated instrument, the THP liquid reagent containing anti-THP-G-6-PDH binds with THP (if present in the urine) in the presence of NAD+ and glucose, NADH will be formed, this corresponding reduction of NAD+ to NADH can be measured quantitatively at 340 nanometers (ultra-violet (UV)). In the alternative, for the analysis of urine for THP on a dipstick, the THP test strip reagent containing anti-THP-Glucose oxidase binds with THP (if present in the urine) in the presence of glucose, peroxidase, and 2,2'-Azinobis(3-ethylbenzthiazoline) sulfonic acid (ABTS, reduced, is colorless chromogenic oxygen acceptor), hydrogen peroxide will be formed from the oxidation of glucose by glucose oxidase, the hydrogen peroxide is then oxidized by the peroxidase and oxygen is given off, the ABTS (present) accepts the oxygen and is oxidized (blue color formed), this corresponding development of color can be measured semi-quantitatively on the dipstick.

4. Chromogenic acceptors or donors—are indicators that are designed to yield a specific color upon binding with or to a reactant, by-product or product of a THP enzymatic or antibody-antigen reaction. Usable chromogenic oxygen, hydrogen or phosphate acceptors or donors as indicators or other compounds that can yield a measurable response by being reduced or oxidized can be part of the linked antibody-antigen complexes, enzymes, or other calorimetric methods, and may include, for example, 4-aminoantipyrine, ABTS, para-Nitrophenyl phosphate, 5-Bromo-4-chloro-3-indoyl phosphate, 3,3',5,5'-Tetramethylbenzidine, ortho-Dianisidine, 5-Aminosalicylic acid, 3,3'-Diaminibenzidine, 3-Amino-9-Ethylcarbazole, 4-Chloro-1-napthol, 4-Chloro-2-methylbenzenediazonium salt, Napthol AS-TR phosphate, Azoalbumin, p-Nitrophenylphosphate, 2,6-dichlorophenol-indophenol, nitrotetrazorium blue, ortho-nitrophenyl, NAD, NADP, NADPH, pyrogallo, para-nitroanilide, hypoxanthine, cytochrome C, uric acid among others. These compounds can also couple with other chemicals (such as phenol) to form dyes.

5. Enzymatic (indicators)—It is known in the art that enzymes to a certain substrate (THP) can be produced in many models (life forms) including animals, plants and bacteria using techniques including but not limited to selection, fermentation, cloning, and gene splicing.

etc. For example, bacterial strains have been selected and cultured to breakdown crude oil as a food source. These bacteria producing certain enzymes that will break down the oils to smaller, consumable constituents (hydrocarbons), and then ingest these break down products. Other similar developments include strains of micro organisms (bacteria) that break down waste products, or produce a specific useful by-product during their metabolism (enzymes, etc.). Utilizing similar techniques micro organisms can be used to produce enzymes that are specific for THP. Fermentation technologies have been used since the 1950's by companies such as TOYOBO Co., LTD. (Japan). This company and others make up a billion dollar a year industry that designs, manufacturers, and markets enzymes that perform a variety of tasks. For instance, TOYOBO manufactures alkalophilic proteinase (an enzyme) from streptomyces sp. in vitro. This enzyme is useful for the proteolysis of a water insoluble protein. The methods utilized to this specific enzyme are described by T. Makanishi, Y. Matsumura, N. Minamiura and T. Yamamoto; Argic. Biol. Chem., 38, 37–44 (1974), and by T. Nakanishi and T. Yamamoto; Agric. Biol. Chem., 38, 2391–2397 (1974) and B. Hagihara, H. Matsubara, M K. Nakai and K. Okunuki; J. Biol. Chem., 45, 185 (1958).

In the case of plants, protein synthesis in choroplasts has been described in the literature for some time. The protein synthesis techniques of chloroplasts more closely resemble that of bacteria than eucaryotic cells see ("The Molecular Biology of the Cell", 2nd Edition, Garland Pyublishing, New York, N.Y.). Furthermore techniques including "recombinant DNA technology that can also utilize Bacteria, yeasts, or mammalia cells which can be engineered to synthesize any desired protein in large quantities" as stated in the "The Molecular Biology of the Cell", (2nd Edition, Garland Publishing, New York, N.Y.; page 196). In 1954, Zamecnik and colleagues developed the first cell-free biological system to carry out protein synthesis. In addition, molecular cloning techniques which are well known in the art can be used to produce large quantities of almost any protein desired. Any of these different techniques can be used to manufacture of enzymes that act specifically on THP, and such methods are well known in the industry and are common knowledge among biologists in the field and have been published. A few references include Struhl,K. and R. W. Davis. 1977. Production of a functional eukaryotic enzyme in *Escherichia coli:* Proc. Natl. Acad. Sci. 74: 5255, Sheppard, H. M., E. Yelverton, and D. V. Goeddel. 1982. Increased synthesis in *E. coli* of fibroblast and leukocyte interferons through alterations in ribosome binding sites. DNA 1: 125. One such mode of THPase production using selection, utilizes a method developed as early as 1961 by a Dr. Charles Hay in a published Master thesis. If one uses the "HAY" protocol, the manufacturer would use THP as the only carbon source available to a variety of strains of bacteria. The colonies that survive would do so only by producing THPase. The surviving colonies would then be cultured and expanded. These colonies would be used to obtain "THPase" (selected to breakdown down THP) which could then be isolated and purified by a method like salting out crystallization (the afore mentioned methods and others can be found in "Outlines of Enzyme Chemistry" 2nd Ed., by Neilands and Stumpf: 1995) for use in assay's for THP. Thus, as explained, the preceeding embodiment adequately describes a process to synthesize the preferred THP enzymes, THP dehydrogenase, THP oxidase, THP hydrolase, THP oxidoreductase and THPase is quite simple and known in the art. These and other THP enzymes can, in the presence of THP, either oxidize, hydrolyze or, dehydrogenate among other modes, the substrate (THP) which can then be measured spectrophotometrically (to include ultra-violet), calorimetrically or by ion-exchange. For example, in the analysis of urine for THP on an automated instrument, the THP liquid reagent containing THP dehydrogenase binds with THP (if present in the urine) in the presence of NAD+, NADH will be formed, this corresponding reduction of NAD+ to NADH can be measured quantitatively at 340 nanometers (ultra-violet (UV)). In the alternative, for the analysis of urine for THP on a dipstick, the THP test strip reagent containing THP oxidase binds with THP (if present in the urine) in the presence of peroxidase, 4-aminoantipyrine (4AAP, is a chromogenic oxygen acceptor), hydrogen peroxide will be formed from the oxidation of THP by THP oxidase, the hydrogen peroxide is then oxidized by the peroxidase and oxygen is given off, the 4AAP (present) accepts the oxygen and forms quinoneimine dye (red color), this corresponding development of color can be measured semi-quantitatively on the dipstick.

Consequently, according to the present invention, there is provided a test strip for the detection of casts in urine, comprising a carrier dipstick containing an indicator compound as discussed above, and according to the present invention, there is provided a liquid reagent for the detection of casts in urine, comprising a carrier-free reagent containing an indicator compound as discussed above.

It was not to have been foreseen that the present technology according to the present invention, would lead to such an extraordinary increase in effectiveness. It is important for the present invention that only urine is specified for the identification of cast.

The effectiveness of the compounds used as indicators according to the present invention is difficult to explain; if, as might be regarded as being obvious, it were due to complex formation with the Tamm-Horsfall glycoprotein.

Surprisingly, the indicators as discussed above increase the sensitivity of a method for the detection of casts exponentially versus manual microscopic analysis, ELISA, gel electrophoresis, two-site immunochemiluminometrics, immunofluorescent staining, zone detection, slide staining, multiple detection layers, etc.

The sensitivity of the detection reaction is increased by the indicators as discussed above to such an extent that even in urine it is possible to detect individual casts which are visible on the test paper as colored dots. Thus, for example, by means of the color indicator, it is possible to produce a test paper with which it is possible clearly to detect 3 to 5 casts per 5.37 uL urine.

It is, of course, obvious that not all of the compounds coming within the scope of general formula (I) possess activating properties of the same degree. Thus, it is possible to adjust the sensitivity of, for example, a urine test in accordance with practical requirements. For example, test strips of increasing activity are obtained when, as activator, there are used the compounds set out in the following and in the given order: antigen-antibody enzyme linked (detected by calorimetric and/or reflectance means), antigen-antibody competitive binding (detected by calorimetric and/or reflectance means), enzymatic (detected by calorimetric, and/or reflectance means), among others.

The sensitivity can be further modified by the use of an antigen-antibody or enzymatic indicator in the liquid chemistry rapid test for cast; thus, for example, by means of an antibody specific for the Tamm-Horsfall (THP) protein, antibody or antigen linked specific for THP, or THP enzyme, or specific compound developed to directly bind with THP and give off a corresponding color development, the specificity and sensitivity of the protein is increased exponentially. The sensitivity limit of a test strip which contains a color indicator may be 3 to 5 casts/5.37 uL urine. The sensitivity, however, for the T-H protein by use of the liquid chemistry rapid test antibody-antigen reaction is 0.1 to 1.35 casts/5.37 ul urine.

The color and ion-exchange indicators can be used in amounts from 0.0005 to 5 g., preferably from 0.01–0.10 g., per 100 ml. of impregnation solution for the dipstick rapid test. The same ranges apply to the liquid chemistry test. The antibody-antigen, antibody-antigen linked or enzyme indicators manufactured from plant, bacterial, animal, or other sources used in the liquid chemistry are diluted 1:250 to 1:10,000 depending on lot specificity of the particular batch of antibody.

Usable buffers, which adjust the pH of the reaction solution to a preferred value also act in this device as compounds that remove interference, may include, for example, a citrate, tris(hydroxymethyl)aminomethane) (TRIS), phosphate, phthalate, acetate, oxalate, succinate buffer, hydrochloric acid, N-2-Hydroxyethylpiperazine-N'-2-ethanesulfonic acid, 2-(N-Morpholino)-ethanesulfonic acid,3-(N-Morpholino)propanesulfonic acid, [Piperazine-N, N'-bis(ethanesulfonic acid)], 3-(Cyclohexylamino)-2-hydroxy-1-propanesulfonic acid, 3-[N,N-bis(hydroxyethyl) amino]-2-hydroxypropanesulfonic acid, Piperazine-N,N'-bis(2-hydroxypropanesulfonic acid), 3-[N-tris-(hydroxymethyl)methy amino]-2-hydroxypropanesulfonic acid, [3-[(1,1-Dimethyl-hydroxyethyl)amino]-2-hydroxypropanesulfonic acid] or others with a pH value and capacity being so chosen that, after dipping the test strip into a urine or adding a specific amount of urine to the liquid chemistry rapid test, the urine matrix is not denatured and a pH value of 2–10 is obtained thereon. The unique ability of the present device to be able to remove matrix interference using a buffer is novel, an example, is a buffer that places the reaction pH at 3.5, the reaction matrix at this pH inactivates any urinary constituents from interfering with the reaction such as urinary enzymes not designed to work at this pH but at a pH of 7.0 in most cases.

Usable chromogenic oxygen, hydrogen or phosphate acceptors or donors as indicators or other compounds that can yield a measurable response by being reduced or oxidized can be part of the linked antibody-antigen complexes, enzymes, or other calorimetric methods, and may include, for example, 4-aminoantipyrine, ABTS, para-Nitrophenyl phosphate, 5-Bromo-4-chloro-3-indoyl phosphate, 3,3',5,5'-Tetramethylbenzidine, ortho-Dianisidine, 5-Aminosalicylic acid, 3,3'-Diaminibenzidine, 3-Amino-9-Ethylcarbazole, 4-Chloro-1-napthol,4-Chloro-2-methylbenzenediazonium salt, Napthol AS-TR phosphate, Azoalbumin, p-Nitrophenylphosphate, 2,6-dichloropehnol-indophenol, nitrotetrazorium blue, ortho-nitrophenyl, NAD, NADP, NADPH, pyrogallo, para-nitroanilide, hypoxanthine, cytochrome C, uric acid among others. These compounds can also couple with other chemicals (such as phenol) to form dyes.

Usable substrates for the components linked to the antibodies-antigens or part of the enzyme substrates or other THP indicators or indicator complex coupling reagents may include, for example, vitamin C, Acyl-CoA, Alcohol, Alkaline phosphatase, cholesterol, choline, creatine, creatinine, formaldehyde, fructose, galactose, glucose, glutamate, 1,2-phenylenediaminehydrochloride, ortho-phenylenediamine, glycerol, lactate, lipoprotein, malate, mannitol, hydrogen peroxide, proline, pyruvate, sarcosine, sorbitol, urea, phenol, xanthine among others.

It is also advantageous to add to the formulation small amounts of about 0.0001–10.0 g. per 100/ml of a complex former (chelator), for example sodium metaphosphate or ethylene-diamine- tetraacetic acid, etc., reducing falsely positive and negative reactions which could be due to traces of metals, thereby interference from an unknown substance being avoided.

Since the test strips, due to the relatively large amount of water soluble substances present therein, could tend to bleed, it is of practical importance to add a thickening agent to the formulation, for example methyl cellulose and, in particular, gelatin, preferably in an amount of about 0.5–5 g. per 100 ml.

As a wetting agent, there is preferably used a long chain organic sulphate or sulphonate, for example sodium dodecyl-benzene sulphonate, BRIJ-35 30% w/v solution of polyoxyethylene ethers, TWEEN 20 polyoxyethylenesorbitan, dioctyl sodium sulphosuccinate or sodium laural sulphate, etc., which are known to stabilize radical cations. The wetting agents can be added to the impregnation solution in amounts of 0.5 to 5 percent, preferably of 1–3 percent. The wetting agents also aid in solubility and reduction of bubbles in solution which is critical in the liquid chemistry rapid test for casts.

For the production of the test strips according to the present invention, absorbent carriers, for example filter paper, cellulose or synthetic resin fleeces, can be impregnated with solutions of the reagents in readily volatile solvents. This is preferably carried out in two separate steps. First, impregnation is carried out with a solution which contains indicator, wetting agent, buffer and optionally a thickening agent and/or solvent. Thereafter, impregnation is carried out with a solution of an indicator and other components necessary to carry out the reaction, again optionally a thickening agent and/or solvent. The indicator may be applied in both steps allowing increase indicator present on the strip to allow for greater sensitivity.

The test strips according to the present invention are, after drying, cut up into strips and preferably sealed between a synthetic resin film and a fine-mesh material in the manner described in German Pat. No, 2,118,455. The present invention, together with the reagents, in a water-stable film in the manner described in U.S. Pat. No. 3,630,957. This has the advantage that the surface of the test strip can, for reading of the color reaction, be cleaned simply by wiping it. For production of the liquid chemistry rapid test for casts according to the present invention, water can be used as the carrier-free solvent for solution of the test ingredients in a volatile or non-volatile liquid medium. This is preferably carried out in two separate steps. First, dissolution is carried out with a liquid medium which contains an indicator, wetting agent, and buffer. The liquid chemistry's according to the present invention are, ready for use upon completion of all the additives being in solution, pH checked, and liquid checked for the presence of any particulate matter, which should be filtered out using a 0.2 to 1.6 micron filter. The following Examples are given for the purpose of illustrating the present invention:

EXAMPLE 1 (preferred)

Filter paper is successively impregnated with the following solutions and dried at 40 degree C.:

Solution I
 1.2M citrate buffer, pH 7.00
 ethylenediamine-tetraacetic acid, disodium salt
 dioctyl sodium sulphosuccinate
 phosphoric acid trimorpholide
 ethanol (solvent)
 and distilled water
Solution 2
 Peroxidase-anti-Tamms-Horsfall protein (linked antibody)
 ABTS (chromogenic oxygen acceptor, color indicator)
 toluene (solvent)
 gelatin (thickener)

(An example of a color indicator in "example 1" is an antibody constituent made up of Peroxidase-anti-Tamm-Horsfall protein (PATHP), when a cast in urine containing Tamm-Horsfall protein reacts with the PATHP the attached peroxidase molecule becomes activated and reacts with the ABTS (color indicator) on the dipstick. The amount of color developed on the dipstick is directly proportional to the amount of cast present in urine. Enzyme-Linked Antibodies are known in the art, this type of methodology depends on conjugation of an enzyme to antibody which is directed at a cellular, protein or tissue antigen. The resulting conjugate is then both immunologically and enzymatically active. A white test paper is obtained which, upon dipping into a casts-containing urine, becomes colored after 5 to 20 seconds. If the casts are intact, then the paper is blue flecked. The sensitivity is about 3 to 5 casts/5.37 uL or the corresponding amount of Tamms-Horsfall protein. A smaller number of intact casts can, under certain circumstances, result in individual dots on the test paper.

EXAMPLE 2

Filter paper is successively impregnated with the following solutions and dried at 37 degree C.:
Solution I
 0.05M TRIS, pH 7.0
 ethanol (solvent)
 gelatin (thickener)
 distilled water
Solution 2
 anti-THP-Glucose oxidase (linked antibody)
 glucose (linked antibody enzyme substrate)
 peroxidase
 4-aminoantipyrine (chromogenic oxygen acceptor)
 phenol (couples with 4AAP to form quioneimine dye)
 toluene (solvent)

(An example of a color indicator mechanism in "example 2" is an antibody constituent made up of anti-THP-Glucose oxidase (ATHPGO), when a cast in urine containing Tamms-Horsfall protein reacts with the ATHPGO the attached oxidase molecule becomes activated and reacts with the glucose present, a by-product of the (glucose) reaction hydrogen peroxide is produced, this in turn is oxidized by peroxidase on the dipstick, the free oxygen given off in this reaction is accepted by 4-aminoantipyrine (chromogenic oxygen acceptor, color indicator), this then in turn binds with phenol to form quinoneimine dye (red). The amount of color (red) developed is directly proportional to the amount of cast present in urine. Enzyme-Linked Antibodies are known in the art, this type of methodology depends on conjugation of an enzyme to antibody which is directed at a cellular, protein or tissue antigen. The resulting conjugate is then both immunologically and enzymatically active. A white test paper is obtained which, upon dipping into a casts-containing urine, becomes colored after 5 to 20 seconds. If the casts are intact, then the paper is red flecked. The sensitivity is about 3 to 5 casts/5.37 uL or the corresponding amount of Tamms-Horsfall protein. A smaller number of intact casts can, under certain circumstances, result in individual dots on the test paper.

EXAMPLE 3

Filter paper is successively impregnated with the following solutions and dried at 37 degree C.:
Solution I
 0.01M TRIS, pH 9.0
 distilled water
Solution 2
 THP yellow
 THPase (An example of a color indicator mechanism in "example 3" is an indicator THP specific, when a cast in urine containing Tamms-Horsfall protein reacts with the THPase, a corresponding lack of color development is measured on the dipstick (competitive binding) versus the color that would have been developed all the THP yellow been metabolized due to the lack of free THP. The amount of color (yellow) developed is directly proportional to the amount of cast present in urine. Enzymes to a specific protein are known in the art, this type of methodology depends on production of a specific enzyme from a source such as bacterial, for example, if THP were put into a media with bacteria as the only source of carbon the bacterium would develop an effective enzyme (THPase) to metabolize the THP over many generations. The bacterium then would be harvested and extracted for the enzyme of interest. A white test strip is obtained which, upon dipping into a casts-containing urine, does not develop color after 5 to 20 seconds. If the casts are intact, then the paper is white flecked. The sensitivity is about 3 to 5 casts/5.37 uL or the corresponding amount of Tamms-Horsfall protein. A smaller number of intact casts can, under certain circumstances, result in individual dots on the test paper.

EXAMPLE 4

Filter paper is successively impregnated with the following solutions and dried at 37 degree C.:
Solution I
 0.05M phthalate, pH 10.0
 ethanol solvent
 distilled water
Solution 2
 ala-THP-polyvinyl chloride
 THPase
 Thymol blue
 toluene (solvent)

(An example of a ion-indicator mechanism in "example 4" is an ala-THP-polyvinyl chloride, when a cast in urine containing Tamms-Horsfall protein reacts with the THPase a corresponding lack of color development is measured on the dipstick (competitive binding) versus the color that would have been developed all the ala-THP-polyvinyl chloride metabolized due to the lack of free THP. The amount of color (blue) developed is directly proportional to the amount of cast present in urine. A white test strip is obtained which, upon dipping into a casts-containing urine, becomes colored after 5 to 20 seconds. If the casts are intact, then the paper is white flecked. The sensitivity is about 3 to 5 casts/5.37 uL or the corresponding amount of Tamm-Horsfall protein. A smaller number of intact casts can, under certain circumstances, result in individual dots on the test paper.

EXAMPLE 5

The automated liquid chemistry reagent is successfully compounded by dissolving the following chemicals at room temperature (25 degree C.):
Solution I
0.05 TRIS buffer, pH 8.0
Urea Hydrogen peroxide
ABTS 0.01%
anti-THP-peroxidase (ATHPP)

(The antibody constituent is made up of anti-THP-peroxidase (ATHPP), when a cast in urine containing Tamm-Horsfall protein reacts with the ATHPP the attached (linked) peroxidase molecule becomes activated and attacks the urea hydrogen peroxide and oxygen is given off and the ABTS (chromogenic oxygen acceptor, color indicator) develops color upon accepting the oxygen present. The amount of color developed in solution is directly proportional to the amount of cast present in urine. This reaction is instantaneous and gives an immediate quantitatively measurable response after only a few seconds (3 to 5). The sensitivity is about 0.1 to 1.35 casts/5.37 uL or the corresponding amount of Tamm-Horsfall protein. A smaller number of intact casts can, under certain circumstances, still bring about a measurable response with the liquid chemistry test. When using the automated liquid chemistries on an autoanalyzer the reagent of Example 3 is placed on an autoanalyzer, then an aliquot of the urine to be tested is placed in an automated analyzer sampling cup, which is placed in a sampling tray within the automated analyzer, the analyzer then transfers urine to a cuvette mounted within the automated analyzer, injects one or more reagent compositions in an aqueous (carrier-free) medium into the cuvette, the reagent composition containing a buffer to adjust the pH of the urine to the preferred pH and remove urinary matrix interference allowing optimization of the reaction (in example 3 the pH is 8.0), and a indicator (in this example the chromogenic reagent is AETS) capable of coupling with oxygen given off from the activated peroxidase (which is linked to the anti-THP) and hydrogen peroxide reaction are mixed then assayed. In the presence of casts this reagent composition is capable of giving a detectable response measured spectrophotometrically at 415 (visible) wavelength in accordance with a preprogrammed code introduced into the automated analyzer (as follows):

| Instrument parameters (Hitachi 717): | |
|---|---|
| CHEMISTRY PARAMETERS | |
| TEST | [URINE CAST] |
| ASSAY CODE | [1 POINT] : [ 0] - [50] |
| SAMPLE VOLUME | [10] |
| R1 VOLUME | [300] [100] [NO] |
| R2 VOLUME | [ 0] [100] [NO] |
| WAVE LENGTH | [700] [415] |
| CALIB. METHOD | [LINEAR] [0] [0] |
| STD. (1) CONC. - POS. | [ 0] - [ 1] |
| STD. (2) CONC. - POS. | [ 1.0] - [ 2] |
| STD. (3) CONC. - POS. | [ 0] - [ 0] |
| STD. (4) CONC. - POS. | [ 0] - [ 0] |
| STD. (5) CONC. - POS. | [ 0] - [ 0] |
| STD. (6) CONC. - POS. | [ 0] - [ 0] |
| SD LIMIT | [ 999] |
| DUPLICATE LIMIT | [32000] |
| SENSITIVITY LIMIT | [ 0] |
| ABS. LIMIT (INC/DEC) | [32000] [INCREASE] |
| PROZONE LIMIT | [ 0] [UPPER] |
| EXPECTED VALUE | [ 0] - [ 1.0] |
| TECH. LIMIT | [ 0] - [ 100] |
| INSTRUMENT FACTOR | [ 1.0] |

Said analyzer determines presence of casts by comparing absorbance at specified wavelength of the patient's urine and reagent composition complex with that of a standard containing a known concentration of Tamm-Horsfall protein and thereby determining the presence or absence of casts in the patient's urine. This device (method) can use a single, or two-reagent composition in an aqueous medium injected into the reaction cuvette. This device (method) reagent composition of Example 5 can contain compounds to neutralize urine matrix interference and increase urine sample reagent compatibility with the automated analyzer, one or more compounds to remove substances in the urine that cause interference with calorimetric photometry, an activating compound that aids in the coupling reaction between casts, THP and anti-THP peroxidase, a surfactant to decrease surface tension and promote mixing on a molecular level and activate the reaction, and a stabilizing agent (such as sodium azide) to prevent color development and stabilize the color indicators or reaction indicators. This device's (method's) wavelength of choice can vary from about 340 to 700 nanometers. Finally, this device (method) for detecting casts in body fluids, comprises contacting a standard or sample of urine, serum, or unknown suspected of containing casts with a reagent composition to detect casts as illustrated for in

EXAMPLE 6

The automated liquid chemistry reagent is successfully compounded by dissolving the following chemicals at room temperature (25 degree C.):
Solution I
0.01 Phosphate, pH 6.0
Glycerol
anti-THP-Glycerol dehydrogenase (ATHPGD)
NAD+

(The antibody constituent is made up of anti-THP-peroxidase (ATHPGD), when a cast in urine containing Tamm-Horsfall protein reacts with the ATHPGD the attached (linked) glycerol dehydrogenase molecule becomes activated and attacks the glycerol and NAD+ is converted to NADH. The amount of NADH developed in solution is directly proportional to the amount of cast present in urine. This reaction is instantaneous and gives an immediate quantitatively measurable response after only a few seconds (3 to 5). The sensitivity is about 0.1 to 1.35 casts/5.37 uL or the corresponding amount of Tamm-Horsfall protein. A smaller number of intact casts can, under certain circumstances, still bring about a measurable response with the liquid chemistry test. When using the automated liquid chemistries on an autoanalyzer the reagent of Example 6 is placed on an autoanalyzer, then an aliquot of the urine to be tested is placed in an automated analyzer sampling cup, which is placed in a sampling tray within the automated analyzer, the analyzer then transfers urine to a cuvette mounted within the automated analyzer, injects one or more reagent compositions in an aqueous (carrier-free) medium into the cuvette, the reagent composition containing a buffer to adjust the pH of the urine to the preferred pH and remove urinary matrix interference allowing optimization of the reaction (in example 4 the pH is 6.0), and a indicator (in this example is NAD+) capable of coupling with hydrogen given off from the activated glycerol dehydrogenase (which is linked to the anti-THP) and glycerol reaction are mixed then assayed. In the presence of casts this reagent composition is capable of giving a detectable response measured spectrophotometrically at 340 (ultra-violet) wavelength in accordance with a preprogrammed code introduced into the automated analyzer (as follows):

| Instrument parameters (Hitachi 717): | |
|---|---|
| CHEMISTRY PARAMETERS | |
| TEST | \|URINE CAST\| |
| ASSAY CODE | \|1 POINT\| : \| 0\| - \|50\| |
| SAMPLE VOLUME | \|10\| |
| R1 VOLUME | \|250\| \|100\| \|NO\| |
| R2 VOLUME | \| 0\| \|100\| \|NO\| |
| WAVE LENGTH | \|700\| \|340\| |
| CALIB. METHOD | \|LINEAR\| \|0\| \|0\| |
| STD. (1) CONC. - POS. | \| 0\| - \| 1\| |
| STD. (2) CONC. - POS. | \| 1.0\| - \| 2\| |
| STD. (3) CONC. - POS. | \| 0\| - \| 0\| |
| STD. (4) CONC. - POS. | \| 0\| - \| 0\| |
| STD. (5) CONC. - POS. | \| 0\| - \| 0\| |
| STD. (6) CONC. - POS. | \| 0\| - \| 0\| |
| SD LIMIT | \| 999\| |
| DUPLICATE LIMIT | \|32000\| |
| SENSITIVITY LIMIT | \| 0\| |
| ABS. LIMIT (INC/DEC) | \|32000\| \|INCREASE\| |
| PROZONE LIMIT | \| 0\| \|UPPER\| |
| EXPECTED VALUE | \| 0\| - \| 1.0\| |
| TECH. LIMIT | \| 0\| - \| 100\| |
| INSTRUMENT FACTOR | \| 1.0\| |

Said analyzer determines presence of casts by comparing absorbance at specified wavelength of the patient's urine and reagent composition complex with that of a standard containing a known concentration of Tamm-Horsfall protein and thereby determining the presence or absence of casts in the patient's urine. This device (method) can use a single, or two-reagent composition in an aqueous medium injected into the reaction cuvette. This device (method) reagent composition of Example 6 can contain compounds to neutralize urine matrix interference and increase urine sample reagent compatibility with the automated analyzer, one or more compounds to remove substances in the urine that cause interference with calorimetric photometry, an activating compound that aids in the coupling reaction between casts, THP and anti-THP glycerol dehydrogenase, a surfactant to decrease surface tension and promote mixing on a molecular level and activate the reaction, and a stabilizing agent (such as sodium azide) to prevent color development and stabilize the color indicators or reaction indicators. This device's (method's) wavelength of choice can vary from about 340 to 700 nanometers. Finally, this device (method) for detecting casts in body fluids, comprises contacting a standard or sample of urine, serum, or unknown suspected of containing casts with a reagent composition to detect casts as illustrated for in EXAMPLE 6.

EXAMPLE 7

The automated liquid chemistry reagent is successfully compounded by dissolving the following chemicals at room temperature (25 degree C.):
Solution I
   0.01 phthalate, pH 10.0
   Cholesterol
   anti-THP-Cholesterol oxidase (ATHPCO)
   peroxidase
   3,3'-Diaminobenzidine (DAB) (chromogenic oxygen acceptor)

(The antibody constituent is made up of anti-THP-Cholesterol oxidase (ATHPCO), when a cast in urine containing Tamm-Horsfall protein reacts with the ATHPCO the attached (linked) cholesterol oxidase molecule becomes activated and attacks the cholesterol and hydrogen peroxide. Peroxidase then attacks the hydrogen peroxide and oxygen is given and accepted by DAB which in turn develops color. The amount of color developed in solution is directly proportional to the amount of cast present in urine. This reaction is instantaneous and gives an immediate quantitatively measurable response after only a few seconds (3 to 5). The sensitivity is about 0.1 to 1.35 casts/5.37 uL or the corresponding amount of Tamm-Horsfall protein. A smaller number of intact casts can, under certain circumstances, still bring about a measurable response with the liquid chemistry test. When using the automated liquid chemistries on an autoanalyzer the reagent of Example 7 is placed on an autoanalyzer, then an aliquot of the urine to be tested is placed in an automated analyzer sampling cup, which is placed in a sampling tray within the automated analyzer, the analyzer then transfers urine to a cuvette mounted within the automated analyzer, injects one or more reagent compositions in an aqueous (carrier-free) medium into the cuvette, the reagent composition containing a buffer to adjust the pH of the urine to the preferred pH and remove urinary matrix interference allowing optimization of the reaction (in example 4 the pH is 6.0), and a indicator (in this example is DAB) capable of coupling with oxygen given off from the activated cholesterol oxidase (which is linked to the anti-THP) and cholesterol reaction are mixed then assayed. In the presence of casts this reagent composition is capable of giving a detectable response measured spectrophotometrically at 660 (visible) wavelength in accordance with a preprogrammed code introduced into the automated analyzer (as follows):

| Instrument parameters (Hitachi 717): | |
|---|---|
| CHEMISTRY PARAMETERS | |
| TEST | \|URINE CAST\| |
| ASSAY CODE | \|1 POINT\| : \| 0\| - \|50\| |
| SAMPLE VOLUME | \|1\| |
| R1 VOLUME | \|250\| \|100\| \|NO\| |
| R2 VOLUME | \| 0\| \|100\| \|NO\| |
| WAVE LENGTH | \|700\| \|660\| |
| CALIB. METHOD | \|LINEAR\| \|0\| \|0\| |
| STD. (1) CONC. - POS. | \| 0\| - \| 1\| |
| STD. (2) CONC. - POS. | \| 1.0\| - \| 2\| |
| STD. (3) CONC. - POS. | \| 0\| - \| 0\| |
| STD. (4) CONC. - POS. | \| 0\| - \| 0\| |
| STD. (5) CONC. - POS. | \| 0\| - \| 0\| |
| STD. (6) CONC. - POS. | \| 0\| - \| 0\| |
| SD LIMIT | \| 999\| |
| DUPLICATE LIMIT | \|32000\| |
| SENSITIVITY LIMIT | \| 0\| |
| ABS. LIMIT (INC/DEC) | \|32000\| \|INCREASE\| |
| PROZONE LIMIT | \| 0\| \|UPPER\| |
| EXPECTED VALUE | \| 0\| - \| 1.0\| |
| TECH. LIMIT | \| 0\| - \| 100\| |
| INSTRUMENT FACTOR | \| 1.0\| |

Said analyzer determines presence of casts by comparing absorbance at specified wavelength of the patient's urine and reagent composition complex with that of a standard containing a known concentration of Tamm-Horsfall protein and thereby determining the presence or absence of casts in the patient's urine. This device (method) can use a single, or two-reagent composition in an aqueous medium injected into the reaction cuvette. This device (method) reagent composition of Example 7 can contain compounds to neutralize urine matrix interference and increase urine sample reagent compatibility with the automated analyzer, one or more compounds to remove substances in the urine that cause interference with calorimetric photometry, an activating compound that aids in the coupling reaction between casts, THP and anti-THP Cholesterol oxidase, a surfactant to decrease surface tension and promote mixing on a molecular level and activate the reaction, and a stabilizing agent (such as sodium azide) to prevent color development and stabilize the color indicators or reaction indicators. This device's (method's) wavelength of choice can vary from about 340 to 700 nanometers. Finally, this device (method) for detecting casts in body fluids, comprises contacting a standard or sample of urine, serum, or unknown suspected of containing casts with a reagent composition to detect casts as illustrated for in EXAMPLE 5.

EXAMPLE 6

The automated liquid chemistry reagent is successfully compounded by dissolving the following chemicals at room temperature (25 degree C.):
Solution I
   0.01 phosphate, pH 5.0
   THP reductase (THPRD) (enzyme)
   NADH (The enzyme constituent is made up of THP reductase (THPRD), when a cast in urine containing Tamm-Horsfall protein reacts with the THPRD and NADH is converted to NAD+. The amount of NAD+ developed in solution is directly proportional to the amount of cast present in urine. This reaction is instantaneous and gives an immediate quantitatively measurable response after only a few seconds (3 to 5). The sensitivity is about 0.1 to 1.35 casts/uL or the corresponding amount of Tamm-Horsfall protein. A smaller number of intact casts can, under certain circumstances, still bring about a measurable response with the liquid chemistry test. When using the automated liquid chemistries on an autoanalyzer the reagent of Example 6 is placed on an autoanalyzer, then an aliquot of the urine to be tested is placed in an automated analyzer sampling cup, which is placed in a sampling tray within the automated analyzer, the analyzer then transfers urine to a cuvette mounted within the automated analyzer, injects one or more reagent compositions in an aqueous (carrier-free) medium into the cuvette, the reagent composition containing a buffer to adjust the pH of the urine to the preferred pH and remove urinary matrix interference allowing optimization of the reaction (in example 4 the pH is 5.0), and the enzyme THPRD, the indicator (in this example is NADH) capable of being oxidized (hydrogen being given off) and converted to NAD+, these are mixed then assayed. In the presence of casts this reagent composition is capable of giving a detectable response measured spectrophotometrically at 340 (ultra-violet) wavelength in accordance with a preprogrammed code introduced into the automated analyzer (as follows):

| Instrument parameters (Hitachi 717): | |
|---|---|
| CHEMISTRY PARAMETERS | |
| TEST | [URINE CAST] |
| ASSAY CODE | \|1 POINT\] : [ 0] - [50] |
| SAMPLE VOLUME | [10] |
| R1 VOLUME | [250] \|100\| [NO] |
| R2 VOLUME | \| 0\|\|100\| [NO] |
| WAVE LENGTH | \|700\| \|340\| |
| CALIB. METHOD | \|LINEAR\| \|0\| \|0\| |
| STD. (1) CONC. - POS. | \| 0\| - [ 1] |
| STD. (2) CONC. - POS. | \| 1.0\| - [ 2] |
| STD. (3) CONC. - POS. | \| 0\| - \| 0\| |
| STD. (4) CONC. - POS. | \| 0\| - \| 0\| |
| STD. (5) CONC. - POS. | \| 0\| - \| 0\| |
| STD. (6) CONC. - POS. | \| 0\| - \| 0\| |
| SD LIMIT | \| 999\| |
| DUPLICATE LIMIT | \|32000\| |
| SENSITIVITY LIMIT | \| 0\| |

| -continued | |
|---|---|
| Instrument parameters (Hitachi 717): | |
| ABS. LIMIT (INC/DEC) | \|32000\| \|INCREASE\| |
| PROZONE LIMIT | \| 0\| \|UPPER\| |
| EXPECTED VALUE | \| 0\| - \| 1.0\| |
| TECH. LIMIT | \| 0\| - \| 100\| |
| INSTRUMENT FACTOR | \| 1.0\| |

Said analyzer determines presence of casts by comparing absorbance at specified wavelength of the patient's urine and reagent composition complex with that of a standard containing a known concentration of Tamm-Horsfall protein and thereby determining the presence or absence of casts in the patient's urine. This device (method) can use a single, or two-reagent composition in an aqueous medium injected into the reaction cuvette. This device (method) reagent composition of Example 6 can contain compounds to neutralize urine matrix interference and increase urine sample reagent compatibility with the automated analyzer, one or more compounds to remove substances in the urine that cause interference with calorimetric photometry, an activating compound that aids in the coupling reaction between casts, THP and THP reductase, a surfactant to decrease surface tension and promote mixing on a molecular level and activate the reaction, and a stabilizing agent (such as sodium azide) to prevent color development and stabilize the color indicators or reaction indicators. This device's (method's) wavelength of choice can vary from about 340 to 700 nanometers. Finally, this device (method) for detecting casts in body fluids, comprises contacting a standard or sample of urine, serum, or unknown suspected of containing casts with a reagent composition to detect casts as illustrated for in EXAMPLE 4.

EXAMPLE 7 (the preferred)

The automated liquid chemistry reagent is successfully compounded by dissolving the following chemicals at room temperature (25 degree C.):
Solution I
   0.01 succinate, pH 3.5
   THP Dehydrogenase (THPDH) (enzyme)
   NAD+

(The enzyme constituent is made up of THP Dehydrogenase (THPDH), when a cast in urine containing Tamm-Horsfall protein reacts with the THPDH and NAD+ is converted to NADH. The amount of NADH developed in solution is directly proportional to the amount of cast present in urine. This reaction is instantaneous and gives an immediate quantitatively measurable response after only a few seconds (3 to 5). The sensitivity is about 0.1 to 1.35 casts/uL or the corresponding amount of Tamm-Horsfall protein. A smaller number of intact casts can, under certain circumstances, still bring about a measurable response with the liquid chemistry test. When using the automated liquid chemistries on an autoanalyzer the reagent of Example 7 is placed on an autoanalyzer, then an aliquot of the urine to be tested is placed in an automated analyzer sampling cup, which is placed in a sampling tray within the automated analyzer, the analyzer then transfers urine to a cuvette mounted within the automated analyzer, injects one or more reagent compositions in an aqueous (carrier-free) medium into the cuvette, the reagent composition containing a buffer to adjust the pH of the urine to the preferred pH and remove urinary matrix interference allowing optimization of the reaction (in example 4 the pH is 5.0), and the enzyme THPDH, the indicator (in this example is NAD+) capable of being reduced (hydrogen being accepted) and converted to NADH, these are mixed then assayed. In the presence of casts this reagent composition is capable of giving a detectable response measured spectrophotometrically at 340 (ultra-violet) wavelength in accordance with a preprogrammed code introduced into the automated analyzer (as follows):

| Instrument parameters (Hitachi 717): | |
| --- | --- |
| CHEMISTRY PARAMETERS | |
| TEST | \|URINE CAST\| |
| ASSAY CODE | \|1 POINT\| : \| 0\| - \|50\| |
| SAMPLE VOLUME | \|3\| |
| R1 VOLUME | \|250\| \|100\| \|NO\| |
| R2 VOLUME | \| 0\| \|100\| \|NO\| |
| WAVE LENGTH | \|700\| \|340\| |
| CALIB. METHOD | \|LINEAR\| \|0\| \|0\| |
| STD. (1) CONC. - POS. | \| 0\| - \| 1\| |
| STD. (2) CONC. - POS. | \| 1.0\| - \| 2\| |
| STD. (3) CONC. - POS. | \| 0\| - \| 0\| |
| STD. (4) CONC. - POS. | \| 0\| - \| 0\| |
| STD. (5) CONC. - POS. | \| 0\| - \| 0\| |
| STD. (6) CONC. - POS. | \| 0\| - \| 0\| |
| SD LIMIT | \| 999\| |
| DUPLICATE LIMIT | \|32000\| |
| SENSITIVITY LIMIT | \| 0\| |
| ABS. LIMIT (INC/DEC) | \|32000\| \|INCREASE\| |
| PROZONE LIMIT | \| 0\| \|UPPER\| |
| EXPECTED VALUE | \| 0\| - \| 1.0\| |
| TECH. LIMIT | \| 0\| - \| 100\| |
| INSTRUMENT FACTOR | \| 1.0\| |

Said analyzer determines presence of casts by comparing absorbance at specified wavelength of the patient's urine and reagent composition complex with that of a standard containing a known concentration of Tamm-Horsfall protein and thereby determining the presence or absence of casts in the patient's urine. This device (method) can use a single, or two-reagent composition in an aqueous medium injected into the reaction cuvette. This device (method) reagent composition of Example 7 can contain compounds to neutralize urine matrix interference and increase urine sample reagent compatibility with the automated analyzer, one or more compounds to remove substances in the urine that cause interference with calorimetric photometry, an activating compound that aids in the coupling reaction between casts, THP and THP Dehydrogenase, a surfactant to decrease surface tension and promote mixing on a molecular level and activate the reaction, and a stabilizing agent (such as sodium azide) to prevent color development and stabilize the color indicators or reaction indicators. This device's (method's) wavelength of choice can vary from about 340 to 700 nanometers. Finally, this device (method) for detecting casts in body fluids, comprises contacting a standard or sample of urine, serum, or unknown suspected of containing casts with a reagent composition to detect casts as illustrated for in EXAMPLE 7.

In closing, to further explain test strip method and use for the determining the presence of Tamm-Horsfall protein in a urine sample, the test strip can comprise of a matrix material comprising a test area impregnated with an indicator reagent selected from the group consisting of ion-exchange, labeled antibody, labeled antigen, chromogenic, Tamm-Horsfall glycoprotein specific and enzymatic indicators and buffers. Also, this test strip for the determining the presence of Tamm-Horsfall protein in the urine sample, can comprise a matrix material comprising a test area impregnated with a indicator reagent selected from the group consisting of ion-exchange, labeled antibody, labeled antigen, chromogenic, and enzymatic indicators, buffers and substrates, and dipping the test strip into the urine sample containing Tamm-Horsfall protein, and determining by measurement of a detectable response by reflectance, visual, colorimetric and spectrophotometric means. This test strip can have series of different types of indicators not to exclude the following, THP specific indicator reagents selected from the group consisting of Tamm-Horsfall red, Tamm-Horsfall blue, Tamm-Horsfall green and Tamm-Horsfall yellow, Tamm-Horsfall ion-exchange indicator reagents selected from the group consisting of Tamm-Horsfall polyvinyl and Tamm-Horsfall ethyleneglycol-bis(beta-aminoethyl ether) N,N,N',N'-tetraacetic acid, and Tamm-Horsfall labeled antibody or antigen indicator reagent labels are selected from the group consisting of nicotinamide adenine dinucleotide phosphate, reduced form (NADPH), nicotinamide adenine dinucleotide phosphate, nicotinamide adenine dinucleotide, nicotinamide adenine dinucleotide, reduced form, glucose-6-phosphate dehydrogenase, alkaline phosphatase, glycerol kinase, beta-delta-galactosidase, C-reactive protein, N-acetylneuraminic acid aldolase, Acyl-CoA oxidase, Acyl-CoA synthetase, Acylpolyamine amidohydrolase, Alcohol oxidase, Alkaline phosphatase, Alkalophilic proteinase, Ascorbate oxidase, cholesterol esterase, cholesterol oxidase, choline oxidase, creatine amidinohydrolase, Creatinine amidohydrolase, creatinine diminase, Diaphorase, Formaldehyde dehydrogenase, delta-Fructose dehydrogenase, Galactose oxidase, beta-Glactosidase, Glucose dehydrogenase, Glucose oxidase, alpha-Glucosidase, beta-Glucosidase, Glutamate dehydrogenase, Glutathione peroxidase, Glucoamlyase, Glycerol dehydrogenase, Glycerol-3-phosphate dehydrogenase, Glycerol kinase, Glycerophosphate oxidase, Hexokinase, para-Hydroxybenzoate hydroxylase, delta-3-Hydroxybutyrate dehydrogenase, Invertase, lactate dehydrogenase, Leucine dehydrogenase, Lipoprotein lipase, Lipase, Amylase, Luciferase, Malate dehydrogenase, Mannitol dehydrogenase, NADPH oxidoreductase, Neuraminidase, Peroxidase, Urease, Uricase, Xanthine oxidase, europium chelate and Protease, and Tamm-Horsfall chromogenic indicator reagents are selected from the group consisting of 4-aminoantipyrine, ABTS, para-Nitrophenyl phosphate, 5-Bromo-4-chloro-3-indoyl phosphate, 3,3',5,5'-Tetramethylbenzidine, ortho-Dianisidine, 5-Aminosalicylic acid, 3,3'-Diaminibenzidine, 3-Amino-9-Ethylcarbazole, 4-Chloro-1-napthol,4-Chloro-2-methylbenzenediazonium salt, Napthol AS-TR phosphate, Azoalbumin, p-Nitrophenylphosphate, 2,6-dichloropehnol-indophenol, nitrotetrazorium blue, ortho-nitrophenyl, NAD, NADP, NADPH, pyrogallo, para-nitroanilide, hypoxanthine, cytochrome C and uric acid, and Tamm-Horsfall enzymatic indicator reagents selected from the group consisting of Tamm-Horsfall protine dehydrogenase, Tamm-Horsfall protein oxidase, Tamm-Horsfall protein hydrolase, Tamm Horsfall protein oxidoreductase and Tamm-Horsfall proteinase, also buffers can be selected from the group consisting of citrate, tris(hydroxymethyl)aminomethane) (TRIS), phosphate, phthalate, acetate, hydrochloric acid, N-2-Hydroxyethylpiperazine-N'-2-ethanesulfonic acid, 2-(N-Morpholino)-ethanesulfonic acid, 3-(N-Morpholino) propanesulfonic acid, [Piperazine-N,N'-bis(ethanesulfonic acid)], 3-(Cyclohexylamino)-2-hydroxy-1-propanesulfonic acid, 3-[N,N-bis(hydroxyethyl)amino]-2-hydroxypropanesulfonic acid, Piperazine-N,N'-bis(2-hydroxypropanesulfonic acid), 3-[N-tris-(hydroxymethyl) methyl amino]-2-hydroxypropanesulfonic acid, [3-[(1,1-Dimethyl-hydroxyethyl)amino]-2-hydroxypropanesulfonic acid], oxalate, citrate and succinate. And substrates can be selected from the group consisting of vitamin C, Acyl-CoA, Alcohol, Alkaline phosphatase, cholesterol, choline, creatine, creatinine, formaldehyde, fructose, galactose, glucose, glutamate, 1,2-phenylenediaminehydrochloride, ortho-phenylenediamine, glycerol, lactate, lipoprotein, malate, mannitol, hydrogen peroxide, proline, pyruvate, sarcosine, sorbitol, urea, phenol, xanthine among others, finally the method for determining the presence of Tamm-Horsfall protein on a test strip impregnated with a Tamm-Horsfall indicator and buffer comprising the steps of dipping a test strip into a urine sample containing Tamm-Horsfall protein and determining the color change by reflectance, visual, calorimetric and spectrophotometric means.

And, to further explain liquid reagent method and use for the determining the presence of Tamm-Horsfall protein in a urine sample, the liquid reagent can comprise of a an indicator reagent selected from the group consisting of ion-exchange, labeled antibody, Tamm-Horsfall glycoprotein specific, labeled antigen, chromogenic, enzymatic indicators and buffers. Also, this liquid reagent for the determining the presence of Tamm-Horsfall protein in the urine sample, can comprise of indicator reagents selected from the group consisting of ion-exchange, labeled antibody, labeled antigen, chromogenic, and enzymatic, buffers and substrates, and determining by color change by reflectance, visual, UV, calorimetric and spectrophotometric (specifically ultra-violet) means. This liquid reagent can have series of different types of indicators not to exclude the following, THP specific indicator reagents selected from the group consisting of Tamm-Horsfall red, Tamm-Horsfall blue, Tamm-Horsfall green and Tamm-Horsfall yellow. Tamm-Horsfall ion-exchange indicator reagents selected from the group consisting of Tamm-Horsfall polyvinyl and Tamm-Horsfall ethyleneglycol-bis(beta-aminoethyl ether) N,N,N',N'-tetraacetic acid, and Tamm-Horsfall labeled antibody or antigen indicator reagent labels are selected from the group consisting of nicotinamide adenine dinucleotide phosphate, reduced form (NADPH), nicotinamide adenine dinucleotide phosphate, nicotinamide adenine dinucleotide, nicotinamide adenine dinucleotide, reduced form, glucose-6-phosphate dehydrogenase, alkaline phosphatase, glycerol kinase, beta-delta-galactosidase, C-reactive protein, N-acetylneuraminic acid aldolase, Acyl-CoA oxidase, Acyl-CoA synthetase, Acylpolyamine amidohydrolase, Alcohol oxidase, Alkaline phosphatase, Alkalophilic proteinase, Ascorbate oxidase, cholesterol esterase, cholesterol oxidase, choline oxidase, creatine amidinohydrolase, Creatinine amidohydrolase, creatinine diminase, Diaphorase, Formaldehyde dehydrogenase, delta-Fructose dehydrogenase, Galactose oxidase, beta-Glactosidase, Glucose dehydrogenase, Glucose oxidase, alpha-Glucosidase, beta-Glucosidase, Glutamate dehydrogenase, Glutathione peroxidase, Glucoamlyase, Glycerol dehydrogenase, Glycerol-3-phosphate dehydrogenase, Glycerol kinase, Glycerophosphate oxidase, Hexokinase, para-Hydroxybenzoate hydroxylase, delta-3-Hydroxybutyrate dehydrogenase, Invertase, lactate dehydrogenase, Leucine dehydrogenase, Lipoprotein lipase, Lipase, Amylase, Luciferase, Malate dehydrogenase, Mannitol dehydrogenase, NADPH oxidoreductase, Neuraminidase, Peroxidase, Urease, Uricase, Xanthine oxidase, europium chelate, 7-amido-4-methylcoumarin and Protease, and Tamm-Horsfall chromogenic indicator reagents are selected from the group consisting of 4-aminoantipyrine, ABTS, para-Nitrophenyl phosphate, 7-amido-4-methylcoumarin 5-Bromo-4-chloro-3-indoyl phosphate, 3,3',5,5'-Tetramethylbenzidine, ortho-Dianisidine, 5-Aminosalicylic acid, 3,3'-Diaminibenzidine, 3-Amino-9-Ethylcarbazole, 4-Chloro-1-napthol,4-Chloro-2-methylbenzenediazonium salt, Napthol AS-TR phosphate, Azoalbumin, p-Nitrophenylphosphate, 2,6-dichloropehnol-indophenol, nitrotetrazorium blue, ortho-nitrophenyl, NAD, NADP, NADPH, pyrogallo, para-nitroanilide, hypoxanthine, cytochrome C and uric acid, and Tamm-Horsfall enzymatic indicator reagents selected from the group consisting of Tamm-Horsfall protein dehydrogenase, Tamm-Horsfall protein oxidase, Tamm-Horsfall hydrolase, Tamm Horsfall protine oxidoreductase and Tamm-Horsfall proteinase, also buffers can be selected from the group consisting of citrate, tris(hydroxymethyl)aminomethane) (TRIS), phosphate, phthalate, acetate, hydrochloric acid, N-2-Hydroxyethylpiperazine-N'-2-ethanesulfonic acid, 2-(N-Morpholino)-ethanesulfonic acid, 3-(N-Morpholino) propanesulfonic acid, |Piperazine-N,N'-bis(ethanesulfonic acid)|, 3-(Cyclohexylamino)-2-hydroxy-1-propanesulfonic acid, 3-|N,N-bis(hydroxyethyl)amino|-2-hydroxypropanesulfonic acid, Piperazine-N,N'-bis(2-hydroxypropanesulfonic acid), 3-|N-tris-(hydroxymethyl) methyl amino|-2-hydroxypropanesulfonic acid, |3-|(1,1-Dimethyl-hydroxyethyl)amino|-2-hydroxypropanesulfonic acid|, oxalate and succinate are selected from the group consisting of citrate, and substrates can be selected from the group consisting of vitamin C, Acyl-CoA, Alcohol, Alkaline phosphatase, cholesterol, choline, creatine, creatinine, formaldehyde, fructose, galactose, glucose, glutamate, 1,2-phenylenediaminehydrochloride, ortho-phenylenediamine, glycerol, lactate, lipoprotein, malate, mannitol, hydrogen peroxide, praline, pyruvate, sarcosine, sorbitol, urea, phenol, xanthine among others, finally the method for determining the presence of Tamm-Horsfall protein on a test strip impregnated with a Tamm-Horsfall indicator and buffer comprising the steps of dipping a test strip into a urine sample containing Tamm-Horsfall protein and determining the color change by reflectance, visual, calorimetric and spectrophotometric means. The method for determining the presence of Tamm-Horsfall protein in a urine comprising placing an aliquot of the urine to be tested in an automated analyzer sampling cup, placing the cup in a sampling tray within the automated analyzer, transferring the urine to a cuvette mounted within the automated analyzer, injecting at least one reagent composition in an aqueous medium into the cuvette, wherein said at least one reagent composition comprises a buffer to adjust the pH of the reaction solution to a preferred pH, a Tamm-Horsfall indicator reagent, reading the aliquot of urine at specified intervals, in accordance with a preprogrammed code introduced into the automated analyzer, at a preprogrammed monochromatically specified wavelength, to compare absorbance of the patient's urine and reagent composition complex with that of a standard containing a known concentration of Tamm-Horsfall protein and thereby determining the presence or absence of cast in the patient's urine.

The previously mentioned methods can be monitored by a spectrophotometer at wavelengths of about 340 to 700 nanometers.

And finally to condense the prior art a method has been described for contacting the urine with Tamms-Horsfall protein specific reagent from a group consisting of Tamms-Horsfall protein labeled antibody, Tamm-Horsfall protein specific, Tamms-Horsfall protein labeled antigen, or Tamms-Horsfall protein enzymes selected from the group consisting of Tamm-Horsfall protein dehydrogenase, Tamm-Horsfall protein oxidase, Tamm-Horsfall protein hydrolase, Tamm Horsfall protein oxidoreductase and Tamm-Horsfall proteinase.

And a method has been previously described for manufacturing Tamm-Horsfall protein enzymes by first introducing Tamm-Horsfall protein to a a variety of strains of micro organisms (bacteria) colonies as the only carbon source available for the organisms to survive on for a food source, then the surviving colonies would then be cultured and expanded, these colonies would be used to obtain Tamm-Horsfall protein enzymes used by the surviving colonies to obtain subsistence for survival, this protein would then be isolated and purified.

It will be understood the specification and examples are illustrative but not limitative of the present invention and that other embodiments within the spirit and scope of the invention will suggest themselves to those skilled in the art.

CITED U.S. Pat. Nos.:
4,575,486
3,961,039
4,446,232
4,786,589
3,603,957

What is claimed is:

1. An immunoassay for determining the presence or amount of casts in a urine sample, said method comprising contacting said urine sample with an antibody which specifically binds to Tamm-Horsfall protein to form an immunocomplex; and, measuring said immunocomplex to determine the presence or amount of said Tamm-Horsfall protein in said urine sample, wherein the presence or amount of said Tamm-Horsfall protein indicates the presence or amount of said casts in said urine sample.

* * * * *